United States Patent
Gunderson et al.

(10) Patent No.: US 10,252,068 B2
(45) Date of Patent: Apr. 9, 2019

(54) REDUCING FALSE POSITIVE LEAD INTEGRITY ALERTS

(71) Applicant: Medtronic, Inc., Minneapolis, MN (US)

(72) Inventors: Bruce D. Gunderson, Plymouth, MN (US); Jian Cao, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 117 days.

(21) Appl. No.: 14/934,542

(22) Filed: Nov. 6, 2015

(65) Prior Publication Data

US 2017/0128734 A1    May 11, 2017

(51) Int. Cl.
| | |
|---|---|
| *A61N 1/39* | (2006.01) |
| *A61B 5/00* | (2006.01) |
| *A61B 5/0452* | (2006.01) |
| *A61B 5/0464* | (2006.01) |
| *A61B 5/0468* | (2006.01) |

(Continued)

(52) U.S. Cl.
CPC .......... *A61N 1/3925* (2013.01); *A61B 5/0452* (2013.01); *A61B 5/0464* (2013.01); *A61B 5/0468* (2013.01); *A61B 5/7203* (2013.01); *A61N 1/3706* (2013.01); *A61N 1/3962* (2013.01); *A61B 2560/0276* (2013.01); *A61N 2001/083* (2013.01)

(58) Field of Classification Search
CPC .... A61N 1/3925; A61N 1/0587; A61N 1/365; A61N 1/3704; A61N 1/3962; A61N 1/3987
USPC ...................................... 607/4, 27
See application file for complete search history.

(56) References Cited

U.S. PATENT DOCUMENTS

| | | |
|---|---|---|
| 5,330,508 A | 7/1994 | Gunderson |
| 5,354,316 A | 10/1994 | Keimel |

(Continued)

FOREIGN PATENT DOCUMENTS

| | | |
|---|---|---|
| WO | 0218009 A1 | 3/2002 |

OTHER PUBLICATIONS

St. Jude Medical. Compilation of Device Programming and Alerting Considerations for Monitoring and Managing Leads. Updated Jul. 8, 2013. Available at http://professional.sjm.com/resources/product-performance/riata-important-info/archive/physician-information/practice-management, accessed Apr. 11, 2013, 4 pages.

(Continued)

*Primary Examiner* — Michael Kahelin
*Assistant Examiner* — Minh Duc Pham

(57) ABSTRACT

An implantable medical device having a sensing module and a control module is configured to receive a cardiac electrical signal and sense events from the cardiac electrical signal received via electrodes carried by a medical electrical lead when the medical electrical lead is coupled to the implantable medical device. The control module coupled is configured to detect non-sustained tachyarrhythmia (NST) episodes based on sensed event intervals and determine if the sensed event intervals during the detected NST episode satisfy oversensing criteria. If the oversensing criteria are satisfied, the control module determines whether the detected NST episode satisfies non-lead related oversensing criteria and withholds a lead integrity alert when the NST episode meeting the oversensing criteria is determined to satisfy non-lead related oversensing criteria.

27 Claims, 7 Drawing Sheets

(51) Int. Cl.
*A61N 1/37* (2006.01)
*A61N 1/08* (2006.01)

(56) References Cited

U.S. PATENT DOCUMENTS

| | | | |
|---|---|---|---|
| 5,507,782 | A | 4/1996 | Kieval et al. |
| 5,545,186 | A | 8/1996 | Olson et al. |
| 5,776,168 | A | 7/1998 | Gunderson |
| 6,317,633 | B1 | 11/2001 | Jorgenson et al. |
| 6,393,316 | B1 | 5/2002 | Gillberg et al. |
| 7,027,856 | B2 | 4/2006 | Zhou et al. |
| 7,031,771 | B2 | 4/2006 | Brown et al. |
| 7,047,083 | B2 | 5/2006 | Gunderson et al. |
| 7,167,747 | B2 | 1/2007 | Gunderson et al. |
| 7,233,825 | B2 | 6/2007 | Jorgenson et al. |
| 7,236,828 | B2 | 6/2007 | Casavant et al. |
| 7,283,863 | B2 | 10/2007 | Gunderson et al. |
| 7,289,851 | B2 | 10/2007 | Gunderson et al. |
| 7,333,855 | B2 | 2/2008 | Gunderson et al. |
| 7,369,893 | B2 | 5/2008 | Gunderson |
| 7,515,961 | B2 | 4/2009 | Germanson et al. |
| 7,567,835 | B2 | 7/2009 | Gunderson et al. |
| 7,783,354 | B2 | 8/2010 | Gunderson |
| 7,797,047 | B2 | 9/2010 | Jorgenson et al. |
| 7,831,304 | B2 | 11/2010 | Cao et al. |
| 8,064,996 | B2 | 11/2011 | Belk et al. |
| 8,072,877 | B2 | 12/2011 | Fredriksson |
| 8,078,277 | B2 | 12/2011 | Gunderson et al. |
| 8,160,684 | B2 | 4/2012 | Ghanem et al. |
| 8,200,322 | B2 | 6/2012 | Ousdigian et al. |
| 8,260,419 | B2 | 9/2012 | Gunderson |
| 8,386,024 | B2 | 2/2013 | Gunderson et al. |
| 8,396,543 | B2 | 3/2013 | Hoeppner et al. |
| 8,437,842 | B2 | 5/2013 | Zhang et al. |
| 8,886,296 | B2 | 11/2014 | Patel |
| 2002/0120307 | A1 | 8/2002 | Jorgenson et al. |
| 2003/0204215 | A1 | 10/2003 | Gunderson et al. |
| 2004/0015197 | A1* | 1/2004 | Gunderson .......... A61B 5/0452 607/27 |
| 2004/0064062 | A1 | 4/2004 | Zhou et al. |
| 2006/0116730 | A1 | 6/2006 | Gunderson |
| 2006/0224075 | A1 | 10/2006 | Gunderson et al. |
| 2007/0123788 | A1 | 5/2007 | Gunderson et al. |
| 2008/0004663 | A1 | 1/2008 | Jorgenson |
| 2008/0161870 | A1 | 7/2008 | Gunderson |
| 2008/0161872 | A1* | 7/2008 | Gunderson .......... A61N 1/3702 607/27 |
| 2008/0161873 | A1 | 7/2008 | Gunderson |
| 2008/0172098 | A1 | 7/2008 | Gunderson |
| 2009/0299201 | A1 | 12/2009 | Gunderson |
| 2009/0299432 | A1 | 12/2009 | Stadler et al. |
| 2010/0023072 | A1 | 1/2010 | Belk et al. |
| 2010/0023084 | A1 | 1/2010 | Gunderson |
| 2010/0113889 | A1 | 5/2010 | Ghanem |
| 2010/0114222 | A1 | 5/2010 | Gunderson et al. |
| 2011/0054558 | A1 | 3/2011 | Gunderson et al. |
| 2011/0196247 | A1 | 8/2011 | Cao et al. |
| 2012/0109240 | A1 | 5/2012 | Zhou et al. |
| 2012/0191153 | A1 | 7/2012 | Swerdlow et al. |
| 2012/0197331 | A1 | 8/2012 | Germanson et al. |
| 2013/0079651 | A1 | 3/2013 | Patel et al. |
| 2013/0079654 | A1 | 3/2013 | Patel et al. |

OTHER PUBLICATIONS

St. Jude Medical. Ellipse ICD ShockGuard Technology Advantage Brochure. 2012. Available at http://pei.ie/PEI/media/PEI-media/PDFs/PDFs_Cardiac/PDFs_Cardiac_Products/ellipse_sgtech_secure_sense.pdf, accessed Nov. 5, 2015, 2 pages.

Cao, et al., "A Fully Automatic, Implantable Cardioverter-Defibrillator Algorithm to Prevent Inappropriate Detection of Ventricular Tachycardia or Fibrillation Due to T-Wave Oversensing in Spontaneous Rhythm", Heart Rhythm Society, vol. 9, No. 4, Apr. 2012, 9 pages.

Medtronic. Lead Integrity Alert. Apr. 2009. Available at http://www.medtronic.com/for-healthcare-professionals/products-therapies/cardiac-rhythrn/therapies/unique-features/lead-integrity-alert/#tab2, accessed Apr. 8, 2013, 2 pages.

Ellenbogen et al., Heart Rhythm Society May 8-11, 2013, "Performance of ICD Lead Integrity Alert for Diagnosis of Endotak Lead Failures" 2 pages; Control Tracking No. 13-A-8460-HRS.

Swerdlow et al., "Abstract 11384: Performance of ICD Lead Integrity Alert for Diagnosis of Riata Lead Failures", Circulation, Nov. 6, 2015, 2 pages.

Ellenbogen et al., "Performance of Lead Integrity Alert to Assist in the Clinical Diagnosis of Implantable Cardioverter Defibrillator Lead Failures: Analysis of Different Implantable Cardioverter Defibrillator Leads", Circulation Arrhythm Electropysiol., 2013, vol. 6; 18 pages.

Swerdlow et al., Heart Rhythm Society May 8-11, 2013, Oversensing in True-Bipolar vs. Integrated Bipolar ICD Leads: Is there a Difference? 2 pages; Control Tracking No. 13-A-8391-HRS.

Blanck et al., "Inappropriate Shocks in Patients with Fidelis® Lead Fractures: Impact of Remote Monitoring and the Lead Integrity Algorithm", Journal of Cardiovascular Electrophysiology, 2011, 8 pages.

Kallinen et al., Lead Integrity Alert Algorithm Decreases Inappropriate Shocks in Patients who have Sprint Fidelis Pace-Sense Conductor Fractures, From the Minneapolis Heart Institute Foundation, Minneapolis, Minnesota. 2010, Heart Rhythm Society, 8 pages.

* cited by examiner

REDUCING FALSE POSITIVE LEAD INTEGRITY ALERTS

TECHNICAL FIELD

The disclosure relates to implantable medical devices and associated methods for detecting a medical electrical lead issue and generating an alert to indicate that a lead issue has been detected.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors.

IMDs may deliver therapy to and/or monitor conditions of a variety of organs, nerves, muscle or tissue, such as the heart, brain, stomach, spinal cord, pelvic floor, or the like. Some IMDs, such as cardiac pacemakers or implantable cardioverter defibrillators (ICDs) monitor a patient's heart activity by sensing cardiac electrical signals to detect an abnormal rhythm. Pacemakers and ICDs may provide therapeutic electrical stimulation to the heart of the patient via electrodes carried by a medical electrical lead coupled to the pacemaker or ICD. The electrical stimulation may include pacing pulses to address abnormal cardiac rhythms such as bradycardia and ventricular tachycardia or cardioversion/defibrillation shocks for treating malignant forms of ventricular tachycardia and ventricular fibrillation. The reliability of an IMD in delivering electrical stimulation pulses to treat abnormal rhythms and sensing electrical physiological signals for monitoring a patient depends at least in part on the integrity of the insulation and the electrical conductors of the medical electrical lead that carries the electrodes used for delivering the therapeutic stimulation pulses and for sensing physiological signals.

SUMMARY

In general, the disclosure is directed to techniques for detecting medical electrical lead issues from a cardiac electrical signal received by an IMD via a medical electrical lead. More particularly, the techniques include detecting episodes of non-sustained tachyarrhythmia (NST) and determining whether each NST episode satisfies oversensing criteria based on an analysis of sensed event intervals that occur during the NST episode. If oversensing criteria are satisfied, additional criteria for detecting non-lead related oversensing are applied. A lead integrity alert is generated only if a predetermined number of NST episodes satisfy the oversensing criteria and do not satisfy non-lead related oversensing criteria. If non-lead related oversensing is identified during one or more of the NST episodes that satisfied the lead related oversensing criteria, the lead integrity alert is withheld.

In one example, the disclosure provides an IMD including a sensing circuit and a control module. The sensing circuit is configured to receive a cardiac electrical signal and sense cardiac events within the cardiac electrical signal. The cardiac electrical signal is received via electrodes carried by a medical electrical lead when the medical electrical lead is coupled to the IMD. The control module is coupled to the sensing circuit and configured to determine a plurality of sensed event intervals, each of the plurality of sensed event intervals is determined as a time interval between two consecutive sensed cardiac events. The control module is further configured to detect a non-sustained tachyarrhythmia (NST) episode based on at least a portion of the sensed event intervals, and determine if the sensed event intervals satisfy oversensing criteria. If the sensed event intervals satisfy the oversensing criteria, the control module is configured to compare the detected NST episode to non-lead related oversensing criteria. The control module is configured to ignore the NST episode for purposes of determining whether to generate a lead integrity alert when the non-lead related oversensing criteria are satisfied and to use the NST episode as part of an NST component of a lead issue detection criteria when the non-lead related oversensing criteria are not satisfied.

In another example, the disclosure provides a method including sensing events from a cardiac electrical signal by a sensing module of an implantable medical device, determining sensed event intervals from the cardiac electrical signal, each of the plurality of sensed event intervals being a time interval between two consecutive ones of the sensed events, detecting a non-sustained tachyarrhythmia (NST) episode based on at least a portion of the sensed event intervals, determining if the sensed event intervals of the NST episode satisfy oversensing criteria, comparing the detected NST episode to non-lead related oversensing criteria if the sensed event intervals satisfy the oversensing criteria, ignoring the NST episode for purposes of determining whether to generate a lead integrity alert when the non-lead related oversensing criteria are satisfied, and using the NST episode as part of an NST component of a lead issue detection criteria when the non-lead related oversensing criteria are not satisfied.

In another example, the disclosure provides a non-transitory computer readable storage medium comprising instructions which when executed by a control module of an implantable medical device cause the implantable medical device to sense events from the cardiac electrical signal by a sensing module of the implantable medical device, determine sensed event intervals between consecutive sensed events, each of the plurality of sensed event intervals being a time interval between two consecutive ones of the sensed events, detect a non-sustained tachyarrhythmia (NST) episode based on at least a portion of the sensed event intervals, and determine if the sensed event intervals satisfy oversensing criteria, if the sensed event intervals satisfy the oversensing criteria, compare the detected NST episode to non-lead related oversensing criteria, and withhold a lead integrity alert if the non-lead related oversensing criteria are satisfied.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, an implantable medical device (IMD) is disclosed that is configured to sense cardiac electrical signals and deliver cardiac electrical stimulation therapies using electrodes coupled to the IMD via a medical electrical lead. The IMD is configured sense cardiac electrical events from the cardiac signal, such as R-waves attendant to the depolarization of the ventricular myocardium. Sensed cardiac events are used for determining a patient's heart rhythm and the need for therapy. The IMD is further configured to detect lead issues, e.g., due to an insulation breach or electrical conductor fracture. A lead issue can cause noise signals in the cardiac electrical signal. These noise signals may be falsely sensed as cardiac electrical events, e.g., R-waves. This oversensing of noise signals as cardiac events caused by a lead issue can lead to a false detection of a fast heart rhythm and can result in unnecessarily delivering anti-tachyarrhythmia therapy, such as an electrical shock or anti-tachycardia pacing. When a lead issue is suspected, a lead integrity alert (LIA) can be generated. An IMD configured to generate a LIA is generally disclosed in U.S. Pat. No. 7,289,851 (Gunderson et al.), incorporated herein by reference in its entirety.

The LIA may be generated based at least in part on detecting non-sustained tachyarrhythmia (NST) episodes. An NST episode may include oversensed events due to a lead issue that is falsely sensed as R-waves occurring at tachyarrhythmia event intervals, leading to a false detection of the NST. Accordingly, if a threshold number of NST episodes are detected, possibly in conjunction with other lead issue detection criteria, a LIA may be generated to allow a clinician to evaluate the patient and take corrective action as needed if a lead issue is confirmed.

In some instances, however, oversensing of other types of signals may occur such as when T-waves are sensed as R-waves or other non-cardiac noise is present in the cardiac electrical signal but is not caused by a lead issue, such as electromagnetic interference (EMI) or myopotentials. Oversensing of cardiac electrical signals and/or oversensing of other non-lead related noise signals could also lead to a false detection of an NST. When other types of oversensing contribute to a falsely detected NST episode, and the NST is counted toward triggering a LIA, a false LIA could be generated. Techniques are disclosed herein to reduce the likelihood of a false LIA due to oversensing of signals that are not lead-related noise signals.

Figure 1:
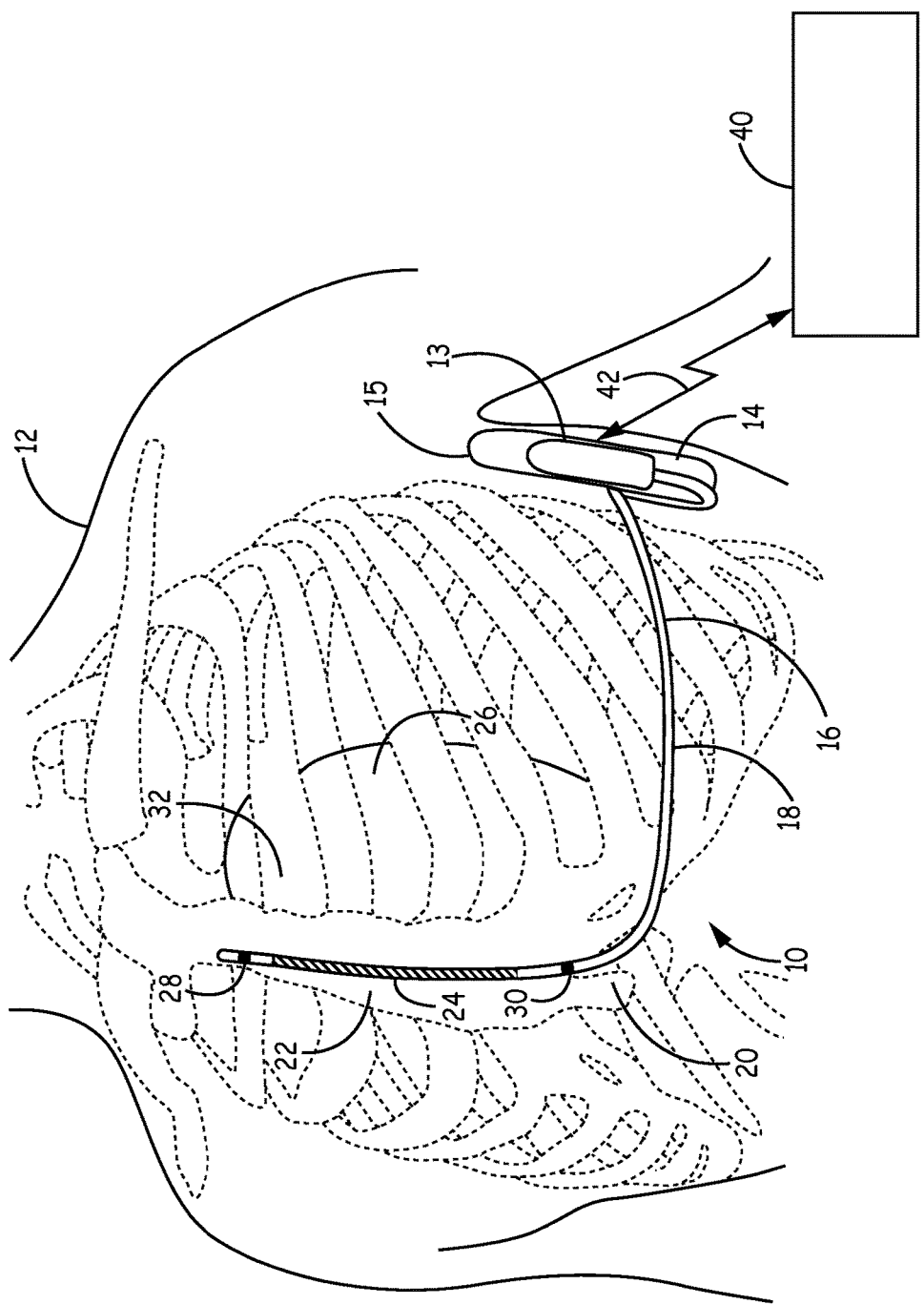
FIG. 1 is a conceptual diagram illustrating one IMD system including an ICD that may be configured to detect a lead issue and generate a lead integrity alert according to the techniques disclosed herein.

FIG. 1 is a conceptual diagram illustrating one IMD system 10 that may be configured to detect a lead issue and generate a LIA according to the techniques disclosed herein. IMD system 10 is used to sense cardiac electrical signals in patient 12 and provide therapy to heart 26. IMD system 10 includes an ICD 14 coupled to an extravascular defibrillation and sensing lead 16. ICD 14 is implanted subcutaneously on the left side of patient 12. Lead 16, which is connected to ICD 14, extends medially from ICD 14 toward sternum 22 and xiphoid process 20 of patient 12. At a location near xiphoid process 20 lead 16 bends or turns and extends subcutaneously superior, substantially parallel to sternum 22. Lead 16 may be implanted such that lead 16 is offset laterally to the left side of the body of sternum 22 (i.e., towards the left side of patient 12), offset to the right of sternum 22 or over sternum 22.

Lead 16 includes a defibrillation electrode 24, which may be an elongated coil electrode, and a pair of sensing electrodes 28 and 30. Lead 16 is placed along sternum 22 such that a therapy vector between defibrillation electrode 24 and the housing 15 of ICD 14 is substantially across one or both ventricles of heart 26. In other examples, another electrode along lead 16 or along a second lead coupled to ICD 14 may be used in combination with defibrillation electrode 24 for delivering a shock therapy.

In the example illustrated in FIG. 1, lead 16 is implanted subcutaneously, e.g., between the skin and the ribcage or sternum. Lead 16 is advanced suprasternally remaining external to the thoracic cavity. In other embodiments, lead 16 may be advanced substernally or within ribcage 32, i.e., intra-thoracically. For example, lead 16 may be implanted at least partially in a substernal location. In such a configuration, a portion of lead 16 may extend subcutaneously from ICD 14 toward sternum 22 and at least the portion of lead 16 carrying electrodes 24, 28 and 30 is advanced under or below the sternum in the mediastinum and, more particularly, in the anterior mediastinum. Lead 16 may be at least partially implanted in other intrathoracic locations, e.g., locations in and around heart 26, with or without making direct contact with the outer surface of heart 26, e.g., in epicardial or pericardial locations. In still other examples, lead 16 may be embodied as a transvenous, intracardiac lead that is advanced transvenously to position one or more electrodes within a patient's heart or its vasculature. An example of an ICD coupled to transvenous medical electrical leads is described below in conjunction with FIG. 3.

Although ICD 14 is illustrated in FIG. 1 as being implanted near a midaxillary line of patient 12, ICD 14 may also be implanted at other subcutaneous locations of patient 12, such as further posterior on the torso toward the posterior axillary line, further anterior on the torso toward the anterior axillary line, in a pectoral region, or at other locations of patient 12. In instances in which ICD 14 is implanted pectorally, lead 16 may follow a different path, e.g., across the upper chest area and inferior along sternum 22. When the ICD 14 is implanted in the pectoral region, lead 16 or a second lead including a defibrillation electrode may extend along the left side of the patient such that a defibrillation electrode is located along the left side of the patient to function as an anode or cathode of a therapy vector for defibrillating heart 26.

The techniques disclosed herein are not limited to a particular implant location of ICD 14 or medical electrical lead 16 coupled to ICD 14. Rather, the disclosed techniques for detecting a lead issue may be implemented in any IMD that is coupled to a medical electrical lead, configured to sense electrical signals via one or more electrodes and electrical conductors carried by the medical electrical lead, and implanted at any desired anatomical location appropriate for a given medical application.

ICD 14 includes a housing 15 that forms a hermetic seal that protects electronic circuitry and other components within ICD 14. The housing 15 of ICD 14 may be formed of a conductive material, such as titanium or other biocompatible conductive material or a combination of conductive and non-conductive materials. In some instances, the housing 15 functions as an electrode (sometimes referred to as a housing electrode or "can" electrode) that is used in combination with one of electrodes 24, 28 and 30 to deliver a therapy to heart 26 or to sense electrical activity of heart 26.

ICD 14 includes a connector assembly 13 (sometimes referred to as a connector block or header) for receiving a proximal connector (not illustrated) of lead 16. Connector assembly 13 includes electrical feedthroughs through which electrical connections are made between electrical conductors within lead 16 and electronic components included within the housing 15.

Lead 16 includes an elongated lead body 18 having a proximal end that includes a connector configured to mate with connector assembly 13 of ICD 14 and a distal portion that includes electrodes 24, 28 and 30. The lead body 18 may be formed from a non-conductive, i.e., electrically insulating material, which may include silicone, polyurethane, fluoropolymers, mixtures thereof, or other appropriate materials, and is shaped to form one or more lumens within which the one or more electrical conductors (not illustrated) each extend to respective ones of electrodes 24, 28 and 30.

When the connector at the proximal end of lead 16 is connected to connector assembly 13, the respective electrical conductors are electrically coupled to circuitry of ICD 14, such as therapy circuit and sensing circuit via connections in connector assembly 13, including associated electrical feedthroughs crossing housing 15. The electrical conductors transmit electrical stimulation pulses from the therapy circuit within ICD 14 to one or more of electrodes 24, 28 and 30 and transmit sensed electrical signals from one or more of electrodes 24, 28 and 30 to the sensing circuit within ICD 14. Although lead 16 is illustrated as including three electrodes 24, 28 and 30, lead 16 may include more or fewer electrodes. For example, two or more sensing electrodes may be included for sensing a cardiac electrical signal, e.g., a subcutaneous electrocardiogram (ECG) signal.

ICD 14 may sense electrical activity of heart 26 from an ECG signal acquired via one or more sensing vectors that include combinations of electrodes 28 and 30 and housing 15. For example, ICD 14 may obtain ECG signals using a sensing vector between electrodes 28 and 30, between electrode 28 and housing 15, between electrode 30 and housing 15, or any combination thereof. In some instances, ICD 14 may even sense cardiac electrical signals using a sensing vector that includes defibrillation electrode 24, such as a sensing vector between defibrillation electrode 24 and one of electrodes 28 and 30, or a sensing vector between defibrillation electrode 24 and the housing 15.

Cardiac electrical signals may be received using any one or more of electrodes 24, 28 and 30 carried by lead 16 for use in detecting NST episodes and for detecting a lead issue when the number of detected NST episodes exceeds a threshold number. In some instances, the number of detected NST episodes is only one of the lead issue detection criteria as described in further detail herein. A lead performance issue may arise if the electrical insulation of a conductor extending to one of electrodes 24, 28 or 30 is breached, if one of the conductors extending through lead body 18 is fractured, or if the electrical connection between the lead connector and ICD connector assembly 13 is compromised. The cardiac electrical signal received by ICD 14 may include noise signals caused by the lead issue. ICD 14 is configured to detect NST, analyze the cardiac electrical signal during the NST to determine sensed event intervals, e.g., RR intervals, and determine whether the sensed event intervals meet oversensing criteria. When the oversensing criteria are met, additional analysis of the cardiac electrical signal may be performed to determine if oversensing due to other, non-lead related causes may be present. If non-lead related oversensing is identified during the NST, the NST episode is not considered in determining whether to trigger an LIA even though oversensing criteria have been met.

In addition to detecting NST, ICD 14 analyzes the acquired ECG signals to detect sustained ventricular tachyarrhythmias (VT). As used herein, the term "VT" refers collectively to ventricular tachyarrhythmias that are detected by ICD 14 as shockable rhythms, which may include ventricular tachycardia and ventricular fibrillation. In response to detecting sustained VT, ICD 14 may generate and deliver an electrical therapy to heart 26. For example, ICD 14 may deliver one or more defibrillation shocks via a therapy vector that includes defibrillation electrode 24 and the housing 15. Oversensing of electrical noise due to a lead issue could lead to a false detection of sustained VT and/or impact therapy delivery.

Accordingly, ICD 14 is configured to detect a lead issue based at least on occurrences of NST such that a LIA may be generated to avoid interference with reliable VT detection due to lead-related noise. ICD 14 may be capable of generating the LIA as a wireless telemetry communication signal transmitted to external device 40 to alert patient 12 or a clinician of the detected lead issue. The wireless telemetry communication signal may be sent to a remote location, e.g., via one or more networks, such as the Medtronic CareLink® Network. In other examples, the LIA may be an audible sound or mild electrical stimulation generated by ICD 14 and perceived by the patient.

ICD 14 is capable of bidirectional wireless communication with external device 40. External device 40 is often referred to as a "programmer" because it is typically used by a physician, technician, nurse, clinician or other qualified user for programming operating parameters in ICD 14. External device 40 may be located in a clinic, hospital or other medical facility. External device 40 may alternatively be embodied as a home monitor or a handheld device that may be used in a medical facility, in the patient's home, or another location. Aspects of external device 40 may generally correspond to the external programming/monitoring unit disclosed in U.S. Pat. No. 5,507,782 (Kieval, et al.), hereby incorporated herein by reference in its entirety.

External device 40 may be used to program operating parameters, such as sensing control parameters, tachyarrhythmia detection control parameters, and therapy delivery control parameters used by ICD 14. Criteria for detecting a lead issue and triggering a LIA may include programmable parameters that can be selected and programmed by a user using external device 40. External device 40 may display programming data and information relating to ICD 14 functions to a user for reviewing ICD operation and programmed parameters as well as ECG signals or other physiological data that are retrieved from ICD 14 during an interrogation session.

External device 40 establishes a wireless radio frequency (RF) communication link 42 with an implantable telemetry module included in ICD 14 for sending and receiving data via communication link 42. Communication link 42 may be established between ICD 14 and external device 40 via a radio frequency (RF) link in the Medical Implant Communication Service (MICS) band, Medical Data Service (MEDS) band, BLUETOOTH® wireless communication standard, Wi-Fi or other RF bandwidth.

External device 40 may be capable of bi-directional communication with ICD 14 over a wide range of distances, e.g., up to approximately 10 meters. In other examples, telemetry communication with ICD 14 may require the use of a programming head placed in proximity of ICD 14 to facilitate data transfer. It is contemplated that external device 40 may be in wired or wireless connection to a communications network for transferring data to a remote database or computer to allow remote management of ICD 14.

Figure 2:
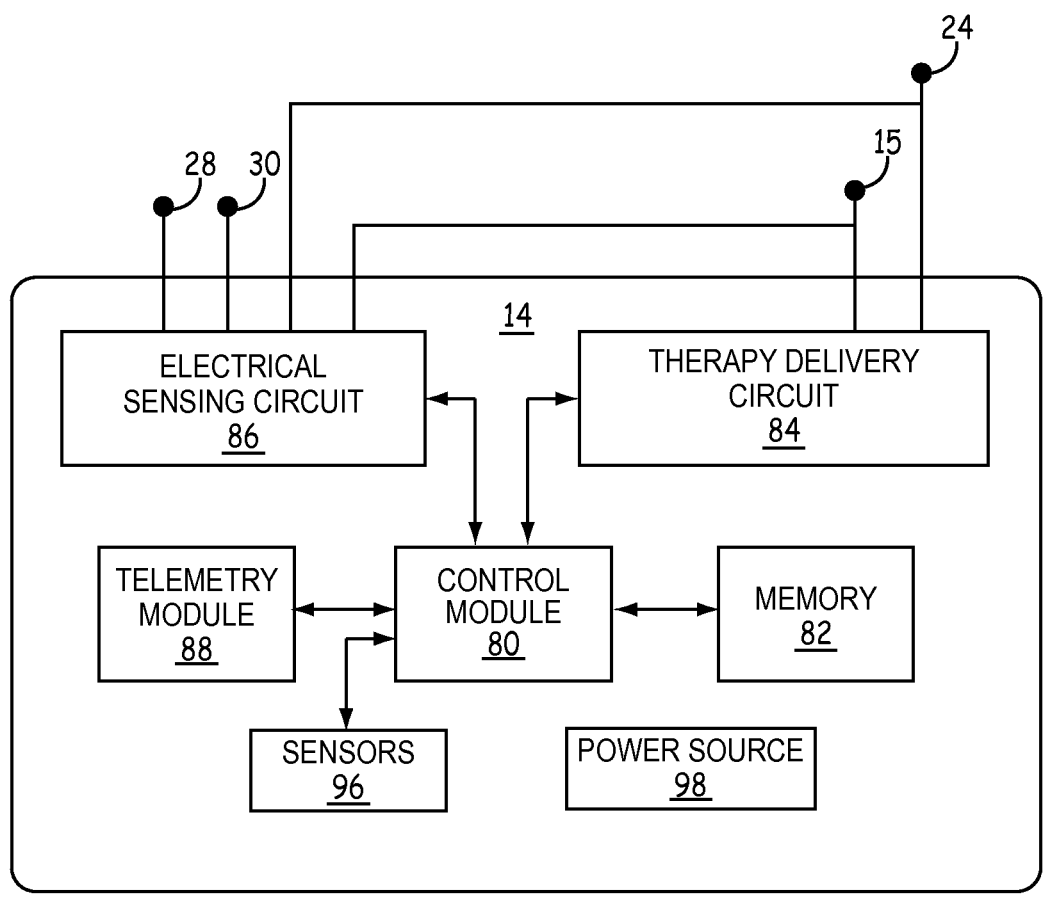
FIG. 2 is a schematic diagram of the ICD of FIG. 1 according to one example.

FIG. 2 is a schematic diagram of ICD 14 according to one example. The electronic circuitry enclosed within housing 15 includes software, firmware and hardware that cooperatively monitor one or more cardiac electrical signals, determine when a cardioversion/defibrillation (CV/DF) shock is necessary, and deliver prescribed CV/DF therapies. ICD 14 is coupled to a lead, such as lead 16 shown in FIG. 1, carrying electrodes, such as electrodes 24, 28 and 30, positioned in operative relation to the patient's heart for sensing cardiac electrical signals and delivering therapeutic electrical stimulation, e.g., CV/DF shocks and post-shock pacing during recovery.

ICD 14 includes control module 80, memory 82, therapy delivery circuit 84, electrical sensing circuit 86, and telemetry module 88. A power source 98 provides power to the circuitry of ICD 14, including each of the modules 80, 82, 84, 86, 88, and 90 as needed. Power source 98 may include one or more energy storage devices, such as one or more rechargeable or non-rechargeable batteries.

The functional blocks shown in FIG. 2 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, processors, application specific integrated circuits (ASICs), memory devices, etc.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14. The non-transitory computer readable media storing the instructions may include any of the media listed above, with the sole exception being a transitory propagating signal.

The functional operation of ICD 14 as disclosed herein should not be construed as reflective of a specific form of software or hardware necessary to practice the methods described. It is believed that the particular form of software, hardware and/or firmware will be determined primarily by the particular system architecture employed in ICD 14. Providing software, hardware, and/or firmware to accomplish the described functionality in the context of any modern IMD system, given the disclosure herein, is within the abilities of one of skill in the art.

Control module 80 communicates with therapy delivery circuit 84 and electrical sensing circuit 86 for sensing cardiac electrical activity, detecting cardiac rhythms, and generating electrical stimulation therapies in response to sensed signals. Therapy delivery circuit 84 is electrically coupled to defibrillation electrode 24 and housing 15 for delivering electrical stimulation therapies such as CV/DF shocks. In some examples, depending on the intended implant location of electrodes 28 and 30, therapy delivery circuit 84 may additionally be coupled to electrodes 28 and 30 for use in delivering therapy and/or delivering mild electrical stimulation for generating a patient alert.

Electrical sensing circuit 86 is electrically coupled to electrodes 24, 28, and 30 carried by lead 16 (shown in FIG. 1) and housing 15, which may serve as a common or ground electrode. Electrical sensing circuit 86 is selectively coupled to sensing electrodes 28, 30 and housing 15 in order to monitor electrical activity of the patient's heart. Electrical sensing circuit 86 may additionally be selectively coupled to defibrillation electrode 24. Sensing circuit 86 may be enabled to monitor one or more sensing vectors selected from the available electrodes 24, 28, 30 and 15. For example, sensing circuit 86 may include switching circuitry for selecting which of electrodes 24, 28, 30 and housing 15 are coupled to sense amplifiers or other cardiac event detection circuitry included in sensing circuit 86. Switching circuitry may include a switch array, switch matrix, multiplexer, or any other type of switching device suitable to selectively couple sense amplifiers to selected electrodes. Sensing circuit 86 may also include one or more sense amplifiers, filters, rectifiers, threshold detectors, comparators, analog-to-digital converters (ADCs), or other analog or digital components.

In some examples, electrical sensing circuit 86 includes multiple sensing channels for sensing multiple ECG sensing vectors selected from electrodes 24, 28, 30 and housing 15. The cardiac event detector of each sensing channel may operate using an auto-adjusting sensing threshold set based on a peak amplitude of a currently sensed event and that may decay over time. Each time the received cardiac electrical signal crosses the auto-adjusting sensing threshold outside an absolute blanking period, a cardiac sensed event signal, such as an R-wave sensed event signal, is produced and passed to control module 80 for use in detecting NST and sustained VT. When noise is present in the cardiac electrical signal, sensed event signals may be produced by sensing circuit 86 in response to sensing noise signals. Accordingly, the cardiac events and/or event intervals may be analyzed by control module 80 to detect evidence of oversensing of non-cardiac noise as well as oversensing of other cardiac events, such as T-wave oversensing and R-wave double counting.

Control module 80 is configured to detect VT episodes that may be life-threatening if left untreated, sometimes referred to as "shockable VT," such as non-sinus, fast ventricular tachycardia or ventricular fibrillation. The timing of R-wave sensed event signals received from sensing circuit 86 may be used by control module 80 to determine sensed event intervals between sensed event signals, e.g., RR intervals. Control module 80 may count sensed event intervals that fall into different rate detection zones for determining a ventricular rate or performing other rate- or interval-based assessments for detecting NST, VT and discriminating VT from rhythms that do not require a CV/DF shock.

Sensing circuit 86 may include an analog-to-digital (A/D) converter for providing a digital ECG signal from one or all available sensing channels to control module 80 for further signal analysis for use in VT detection and analysis of NST episodes. A sensed ECG signal may be converted to a multi-bit digital signal by sensing circuit 86 and provided to control module 80 for performing ECG morphology analysis. Analysis of the ECG signal morphology may be performed for detecting, confirming or discriminating VT.

Examples of algorithms that may be performed by ICD 14 for detecting, discriminating and treating VT are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety. Methods disclosed herein for detecting a lead issue may be implemented in any of the IMDs described in the incorporated references as being coupled to a medical electrical lead.

It should be noted that implemented arrhythmia detection algorithms may utilize not only cardiac electrical signal analysis methods but may also utilize supplemental sensors 96, such as blood pressure, tissue oxygenation, respiration, patient activity, heart sounds, and the like, for contributing to a decision by control module 80 to apply or withhold a therapy.

In some examples, analysis of the cardiac electrical signal by control module 80 is performed to detect NST and determine if sense event intervals during the NST satisfy lead issue detection criteria. Control module 80 may store the cardiac electrical signal received during the NST episode for post-processing to determine if evidence of non-lead related oversensing is present when the NST meets lead issue detection criteria used for triggering a LIA. Examples of the analysis of the cardiac electrical signal received during a detected NST episode for use in triggering or withholding a LIA are described below in conjunction with FIGS. 4, 5, and 8.

Therapy delivery circuit 84 includes a high voltage (HV) therapy delivery module including one or more HV output capacitors and, in some instances, a low voltage therapy delivery module. When a shockable VT rhythm is detected, control module 80 controls the therapy delivery circuit 84 to charge the HV capacitors to a pre-programmed voltage level by a HV charging circuit, which may include one or more capacitors, resistors, inductors, transformers, switches, or other analog or digital components. Control module 80 applies a signal to trigger discharge of the HV capacitors upon detecting a feedback signal from therapy delivery circuit 84 that the HV capacitors have reached the voltage required to deliver a programmed shock energy. In this way, control module 80 controls operation of the high voltage output circuit of therapy delivery circuit 84 to deliver high energy CV/DF shocks using defibrillation electrode 24 and housing 15. Therapy deliver circuit 84 may thus include discharging circuitry to deliver CV/DF, including, for example, an H-bridge circuit.

Control module 80 may be configured to generate a LIA in response to lead issue detection criteria being met. As will be described in detail herein, the lead issue detection criteria include at least an NST component within the lead issue detection criteria. Other components of the lead issue detection criteria may include, but not be limited to, a short interval counter (SIC) component and/or lead impedance component in one example. As described above, the alert may be a communication signal transmitted by telemetry module 88, mild electrical stimulation delivered by therapy delivery circuit 84 via any of electrodes 24, 28, 30 or 15, an audible alert generated by an acoustic transducer included in sensors 96 or other alert signal perceptible by the patient or transmitted to and received by an external device such as device 40 of FIG. 1.

User-programmable sensing and therapy delivery control parameters, including programmable lead issue detection control parameters, may be programmed into memory 82 via telemetry module 88. Telemetry module 88 includes a transceiver and antenna for communicating with external device 40 (shown in FIG. 1) using RF communication. Telemetry module 88 may receive downlink telemetry from and send uplink telemetry to external device 40.

NST episode data may be stored in memory 82 and transmitted by telemetry module 88 to external device 40 upon receipt of an interrogation command. Clinician or technician review of NST episodes facilitates proper diagnosis of a lead issue, enabling corrective action to be taken, such as reprogramming ICD 14 to use different therapy and/or sensing vectors, replacement of lead 16, or adjustment of the connection between lead 16 and ICD 14.

Figure 3:
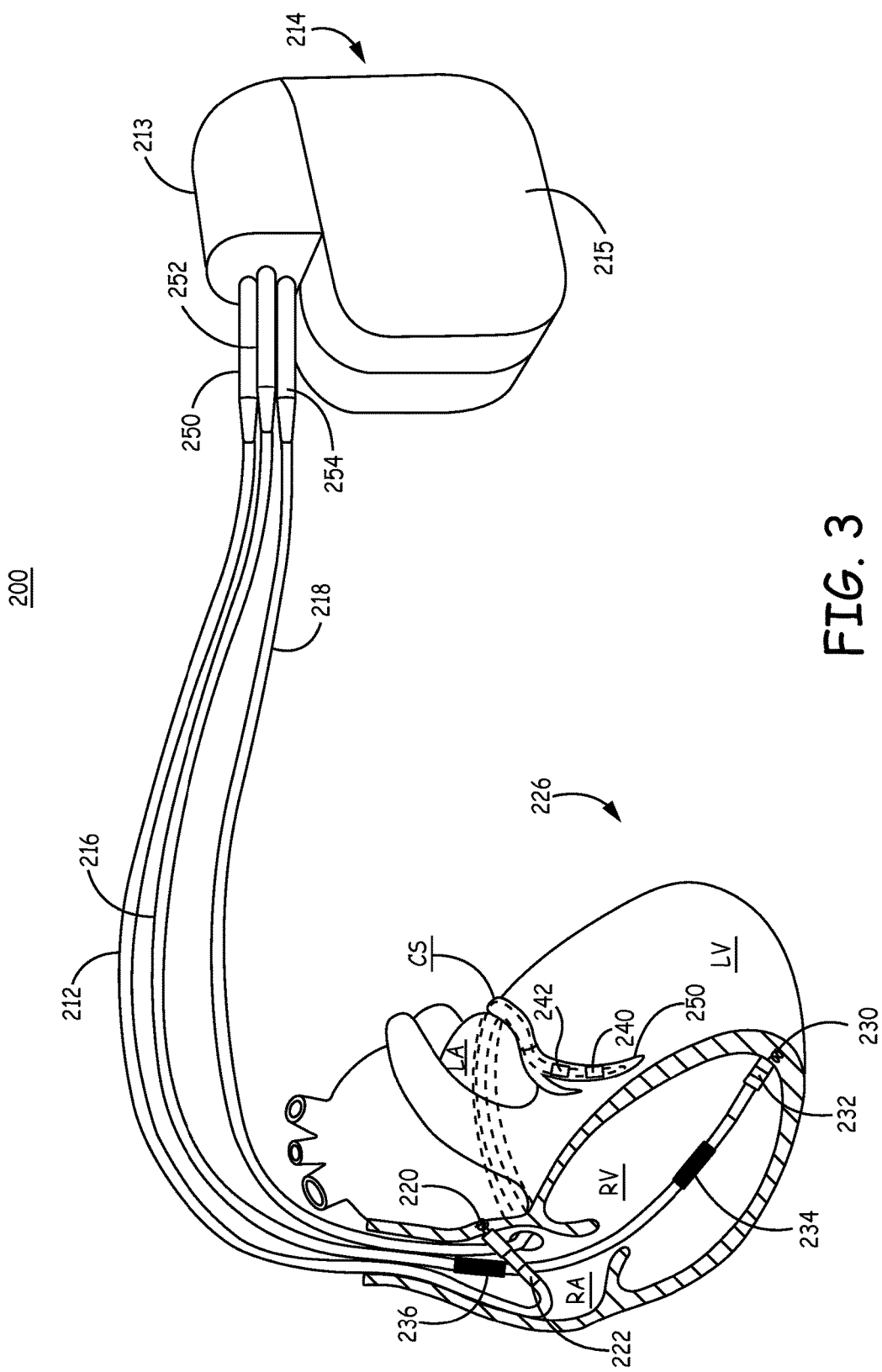
FIG. 3 is a schematic representation of an alternative IMD system that may be configured to detect a lead issue and generate a lead integrity alert.

FIG. 3 is a schematic representation of an IMD system 200 that includes an ICD 214 capable of delivering high voltage and low voltage therapies to heart 226. The presently disclosed techniques for generating a LIA based at least on the detection and analysis of NST episodes may be implemented in IMD system 200, which includes transvenous lead(s) that extend into heart 226.

ICD 214 is coupled to heart 226 via leads 212, 216, and 218. Right atrial lead 212 extends from ICD 214 to the right atrium (RA) and carries distal electrodes 220 and 222 for sensing cardiac electrical signals and delivering pacing pulses in the RA. In addition, ICD housing 215 may be used as a return electrode in combination with electrodes 220 and/or 222 to deliver the pacing pulses in the RA.

Right ventricular lead 216 carries a tip electrode 230 and a ring electrode 232 for sensing cardiac electrical signals and delivering pacing pulses in the RV. RV lead 216 may additionally carry high voltage electrodes 234 and 236, referred to herein as the RV defibrillation electrode 234 and the superior vena cava (SVC) defibrillation electrode 236, for delivering high voltage CV/DF shocks in response to detecting a shockable VT from sensed cardiac signals. Housing 215 may be used with pace/sense electrodes 230 and 232 for delivering RV pacing pulses or in combination with defibrillation electrodes 234 and/or 236 during shock delivery.

A coronary sinus (CS) lead 218 is shown extending into a cardiac vein 250 via the RA and coronary sinus for positioning electrodes 240 and 242 for sensing cardiac signals and delivering pacing pulses along the left ventricle (LV). In some examples, CS lead 218 may additionally carry electrodes for positioning along the left atrium (LA) for sensing and stimulation along the left atrial chamber. CS lead 218 may carry additional electrodes positioned along the left ventricle, e.g., four electrodes or more for providing multiple selectable pacing or sensing vectors. Housing 215 may be used as an electrode in combination with electrodes 240 and/or 242 to deliver the pacing pulses to the LV.

The depicted positions of leads 212, 216 and 218 in or about the right and left heart chambers are merely illustrative. Other leads and pace/sense electrodes and/or high voltage CV/DF electrodes can be used instead of, or in combination with, any one or more of the depicted leads and electrodes shown in FIG. 3. ICD 214 is shown as a multi-chamber device capable of sensing and stimulation in three or all four heart chambers. It is understood that ICD 214 may be modified to operate as a single chamber device, e.g., with a lead positioned in the RV only, or a dual chamber device, e.g., with a lead positioned in the RA and a lead positioned in the RV.

In general, ICD 214 may be embodied as any single, dual or multi-chamber device configured to receive at least one medical electrical lead by a connector assembly 213 having one or more bores for mating with a respective number of lead connectors. Electrodes carried by a lead coupled to ICD 214 are used for sensing cardiac electrical signals and for delivering shock therapy to heart 226. ICD 214 may be embodied as an ICD capable of delivering both low voltage pacing pulses, e.g., for bradycardia pacing, anti-tachycardia pacing, etc., and high voltage CV/DF shocks.

Each of leads 212, 216 and 218 include insulated electrical conductors extending from the respective electrodes 220, 222, 230, 232, 234, 236, 240 and 242 to a respective proximal connector 250, 252, or 254 that electrically couples the electrodes to circuitry enclosed by housing 215 when the proximal connectors 250, 252 and 254 are properly positioned in IMD connector assembly 213. Circuitry enclosed in housing 215 may generally correspond to the modules and their associated functions shown and described in conjunction with FIG. 2 above. Instead of electrodes 24, 28 and 30 as shown in FIG. 2, electrodes 220, 222, 230, 232, 234, 236, 240 and 242 may be selectively coupled to electrical sensing circuit 86 via switching circuitry in which case sensing circuit 86 may include multiple sensing channels, e.g., a RA sensing channel, RV sensing channel and LV sensing channel. Electrodes 220, 222, 230, 232, 234, 236, 240 and 242 may be coupled to therapy delivery circuit 84 for delivering low voltage pacing pulses for providing bradycardia pacing, cardiac resynchronization therapy (CRT) or anti-tachycardia pacing (ATP) to the respective heart chambers or for delivering shock therapy.

Figure 4:
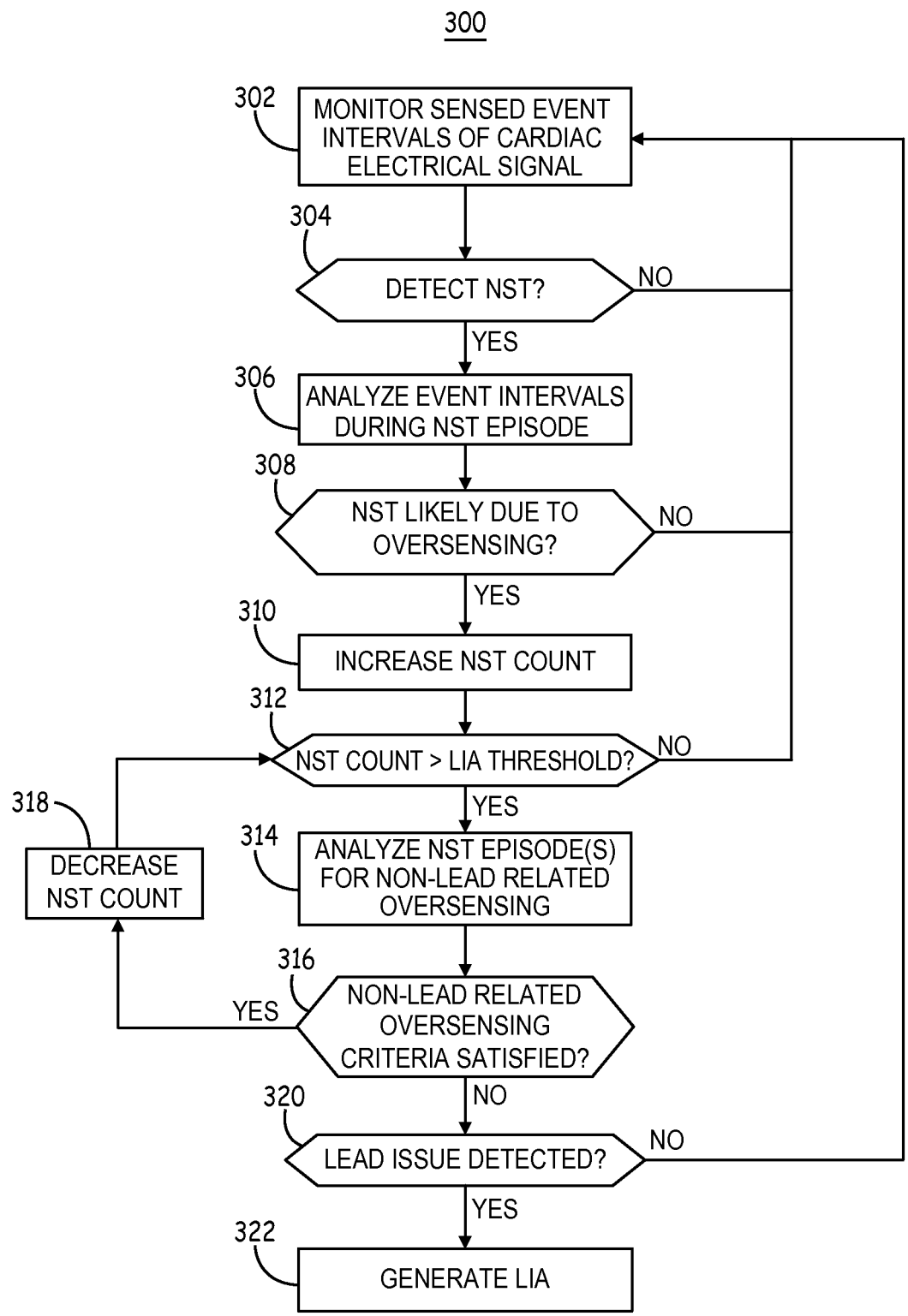
FIG. 4 is a flow chart of one example method for detecting a lead issue and generating a lead integrity alert based on detection and analysis of non-sustained tachyarrhythmia episodes.

FIG. 4 is a flow chart 300 of one example method for detecting a lead issue and generating a LIA based at least on detection and analysis of NST episodes. At block 302, control module 80 determines intervals between cardiac events within sensed cardiac electrical signals received from sensing circuit 86. The sensed event intervals are monitored by the control module 80 by comparing event intervals to predetermined tachyarrhythmia intervals. The cardiac events sensed within the cardiac electrical signals received from sensing circuit 86 may be sensed R-wave events such that RR intervals are monitored at block 302. In other examples, the sensed cardiac events may be P-wave sensed events such that PP intervals are monitored at block 302. In still other examples, sensed event intervals monitored at block 302 may include RR intervals, PP intervals, P-R intervals R-P intervals or any combination thereof for use in detecting event intervals that are indicative of a tachyarrhythmia.

The sensed event intervals are monitored at block 302 to determine if an NST is detected at block 304 according to NST detection criteria. For example, event intervals may be compared to a tachyarrhythmia detection interval threshold for detecting tachyarrhythmia intervals. A tachyarrhythmia detection interval may be set to 320 ms or other desired interval according to patient need. A sensed event interval shorter than the tachyarrhythmia interval is counted as a tachyarrhythmia interval. NST detection criteria may be satisfied when a minimum number of tachyarrhythmia intervals is reached without reaching the required number of intervals to detect a sustained tachyarrhythmia episode. In an illustrative example, the number of tachyarrhythmia intervals to detect a sustained tachyarrhythmia, sometimes referred to as "NID" or number of intervals to detect, may be 18 tachyarrhythmia intervals out of 24 consecutive sensed event intervals. An NST may be detected when a required number of tachyarrhythmia intervals is reached that is less than the NID and the NID is not satisfied. Tachyarrhythmia intervals are counted by control module 80 during monitoring at block 302, and if the interval count reaches an NST detection threshold at block 304, e.g., at least five consecutive tachyarrhythmia intervals without satisfying the NID, NST is detected at block 304. Using the example VT detection criteria of 18 tachyarrhythmia intervals out of 24 consecutive sensed event intervals given above, the next nineteen sensed event intervals following the five consecutive tachyarrhythmia intervals may include fewer than thirteen tachyarrhythmia intervals such that a sustained VT detection is not made. The five consecutive tachyarrhythmia intervals are detected as an NST episode.

If the NST detection criteria are not satisfied, the control module 80 continues to monitor the sensed event intervals at block 302. It is recognized that in some examples, detection of an NST episode may additionally or alternatively include monitoring the waveform morphology of the sensed events at block 302 for use in identifying sensed events as tachyarrhythmia events.

In response to detecting an NST episode at block 304, control module 80 may analyze the sensed event intervals during the NST episode at block 306 to determine whether the NST is likely caused by oversensing. For example, the sensed event intervals during the NST episode may be analyzed by determining at least one event interval metric and comparing the event interval metric(s) to an oversensing criteria. The event interval metric(s) determined for detecting possible oversensing may include a maximum, minimum, range, or average of the sensed event intervals during the NST episode. One or more of these event interval metrics may be compared to a respective threshold or other criteria for detecting that the NST is likely caused by oversensing.

For example, the range of sensed event intervals during an NST that is likely caused by oversensing is expected to be greater than the range of sensed event intervals during a true NST. As such, at least one metric determined at block 306 may be the range of all the sensed event intervals occurring during the detected NST episode. This range may be compared to a threshold range at block 308. If the range is greater than the threshold range, NST due to oversensing is detected at block 308. Examples of criteria that may be applied to sensed event interval metrics at block 308 for determining whether to count an NST episode toward the detection of a lead issue and generating a LIA are described in U.S. Pat. No. 8,260,419 (Gunderson), incorporated herein by reference in its entirety.

If the event interval metric(s) meet the oversensing criteria, as determined at block 308, control module 80 may increase an NST counter at block 310. The NST episodes that satisfy the oversensing criteria applied at block 308 are counted toward triggering the generation of a LIA. If the NST count reaches a threshold for generating a LIA, as determined at block 312, control module 80 performs additional analysis of the cardiac electrical signal acquired during the counted NST episode(s) at block 314 to determine if evidence of non-lead related oversensing is present in the counted NST episodes.

It is recognized that the NST counter may be a running counter that may be decreased if a required number of NST episodes satisfying the oversensing criteria is not reached within a predetermined time period. The decision made at block 312 may require the NST count to reach a threshold count within a predetermined time period, e.g., 24 hours, 3 days, one week or other selected time interval. Older NST episodes may be discarded to count the number of NST episodes satisfying the oversensing criteria within the most recent predetermined time period.

The oversensing criteria applied at block 308 to the event intervals during the NST episode may successfully result in identifying all NST episodes that include oversensing. In some cases, however, oversensing that causes the oversensing criteria to be satisfied at block 308 may actually be non-lead related oversensing. Oversensed events that are not due to a lead issue but cause the sensed event intervals to meet the oversensing criteria could lead to false detection of a lead issue and generation of a false LIA.

Accordingly, after the NST episode is detected and determined to meet the lead related oversensing criteria at block 308, further analysis of the cardiac electrical signal acquired during the NST episode is performed at block 314 to rule out the presence of non-lead related oversensing before triggering the LIA. In some examples, the analysis performed at block 314 for identifying whether an NST is caused by non-lead related oversensing is only performed after the NST episode count reaches a threshold for generating a LIA. Processing burden is reduced by performing the additional analysis for identifying non-lead related oversensing only when all other criteria for detecting a lead issue and triggering a LIA are satisfied. When an NST episode is determined to satisfy the oversensing criteria at block 308, the cardiac electrical signal received during the NST episode may be stored in memory 82 to be available for post-processing by control module 80 at block 314 if the LIA NST count is reached at block 312. In other examples, the analysis performed at block 314 for identifying whether an NST is caused by non-lead related oversensing may be performed each time an NST episode is detected and the NST. In this example, blocks 314 and 316 may be performed prior to blocks 310 and 312.

Control module 18 may analyze each NST episode contributing to the LIA NST count for evidence of non-lead related oversensing before generating a LIA. As such, if the currently detected NST episode fails to satisfy non-lead related oversensing criteria, a preceding NST episode counted by the NST counter and contributing to the LIA threshold being reached may be analyzed at block 314 for non-lead related oversensing. In some examples, if any of the NST episodes that caused the NST count to be increased satisfies the non-lead related oversensing criteria at block 316, the NST component of the lead issue detection criteria may be withheld and the NST count may be decremented at block 318 by the number of NST episodes determined to satisfy the non-lead related oversensing criteria.

Non-lead related oversensing may include cardiac oversensing and/or non-cardiac, non-lead related oversensing. Cardiac oversensing is incorrect sensing of a signal arising from the heart as a particular cardiac event. Cardiac oversensing may include T-wave oversensing (TWOS) where T-waves are incorrectly sensed as R-waves, R-wave double-counting where a single R-wave is sensed twice, and/or P-wave oversensing, where a P-wave is sensed as an R-wave. Non-cardiac, non-lead related oversensing may include oversensing of electromagnetic interference (EMI) and non-cardiac, myopotential noise. Analysis of the cardiac signal during the NST episode for evidence of non-lead related oversensing at block 316 may include analyzing sensed event intervals, analyzing the amplitude or waveform of the sensed events, and/or analyzing the cardiac electrical signal between sensed events. Analysis that may be performed at block 316 is described in conjunction with FIG. 5.

If non-lead related oversensing is identified during one or more NST episodes that were counted toward reaching the LIA NST, as determined at block 316, the NST component of the lead issue detection criteria will not be met, thus reducing the likelihood of falsely a lead issue.

If the non-lead related oversensing criteria are not satisfied at block 316 (e.g., none of the NST episodes satisfy the non-lead related oversensing criteria), the NST component of the lead issue detection criteria is satisfied. At block 320, control module 80 may determine whether all lead issue detection criteria are satisfied. Lead issue detection criteria may require a threshold count of NST episodes that do not include non-lead related oversensing. It is to be understood that in some examples other lead issue detection criteria may be utilized and applied at block 320, such as lead impedance measurement criteria or other oversensing criteria, in combination with the NST count in detecting a lead issue. If a lead issue is confirmed at block 320, a LIA is generated at block 322. Once a LIA is generated, the process shown by FIG. 4 may be terminated until re-enabled by a user, e.g., after the lead issue has been resolved. In other examples, control module 80 may repeat the process of flow chart 300 and deliver repeated LIAs until disabled by a user or a corrective action has been taken.

In flow chart 300, analysis for non-lead related oversensing (block 314) is not performed until after the NST counter reaches the LIA threshold (block 312) to avoid signal processing that may not be required should the NST counter never reach the LIA threshold. In other examples, the analysis of the NST episode for non-lead related oversensing criteria (block 316) may be performed when the NST episode is found to satisfy the oversensing criteria and before the NST count is increased at block 310. The NST count may be increased once the oversensing criteria are satisfied and the non-lead related oversensing criteria are not satisfied for the detected NST episode. Whether the analysis of the NST episode for identifying non-lead related oversensing is performed before or after adjusting the NST count, identification of non-lead related oversensing during an NST episode that otherwise satisfies oversensing criteria results in the NST component of the lead issue detection criteria not being satisfied as the NST count is either never incremented by those particular NST episodes or the NST count is decremented upon detecting those NST episodes.

Figure 5:
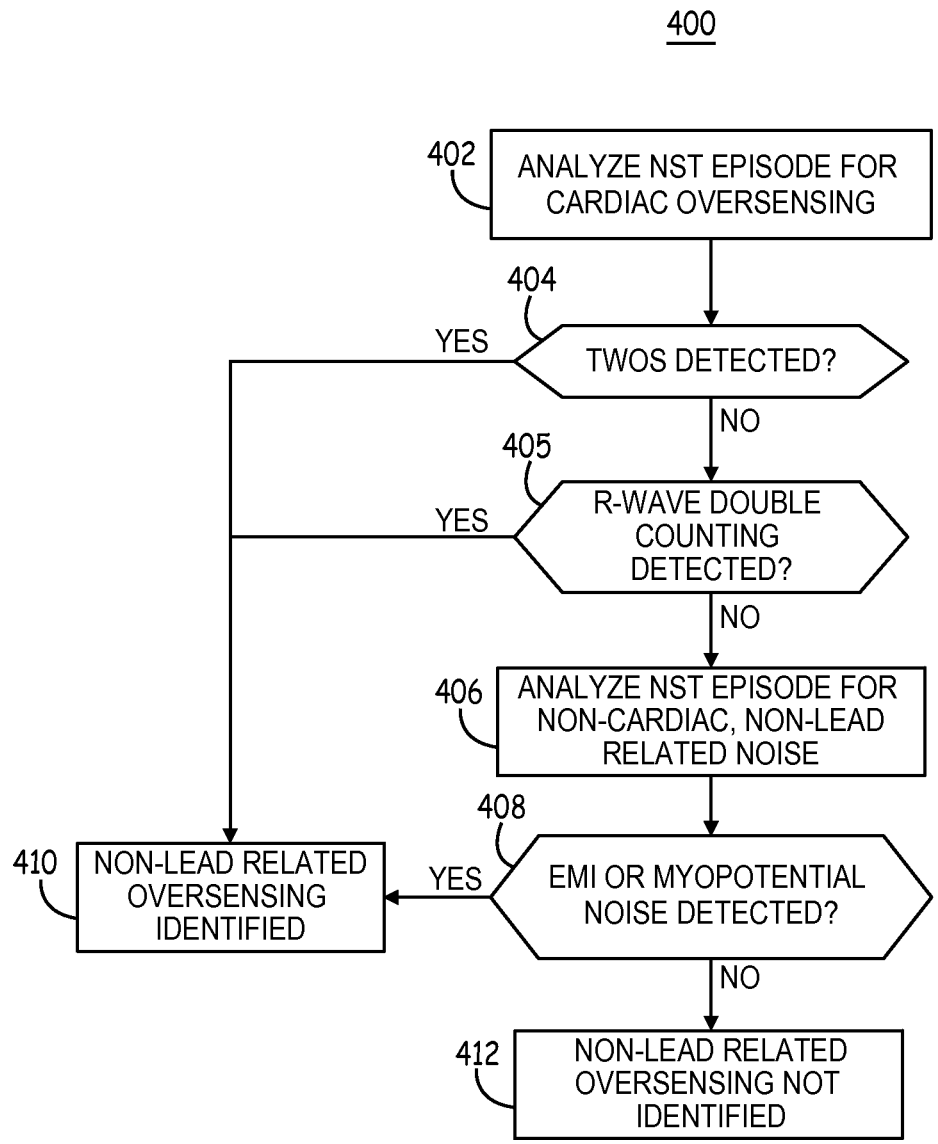
FIG. 5 is a flow chart of an example method for identifying non-lead related oversensing during a detected non-sustained tachyarrhythmia episode.

FIG. 5 is a flow chart 400 of an example method for identifying non-lead related oversensing that is present in a detected NST episode determined to likely be caused by oversensing. Methods included in flow chart 400 may be performed at blocks 314 and/or 316 of FIG. 4 for identifying non-lead related oversensing after the sensed event intervals of an NST episode satisfy the oversensing criteria (e.g., after block 312 of FIG. 4) or after a detected NST episode is determined to be likely caused by oversensing (e.g., after block 308 of FIG. 4).

At block 402, control module analyzes the NST episode for cardiac oversensing. Sensed events during the NST episode are analyzed for oversensing of cardiac events, such as TWOS and R-wave double counting. To identify TWOS, the peak amplitudes and/or morphology of each sensed event during the NST episode may be determined and compared to identify alternating patterns of amplitude or morphology that would discriminate oversensed T-waves from true R-waves. Example methods that may be used for detecting TWOS are generally disclosed in U.S. Pat. No. 7,831,304 (Cao, et al.) and in U.S. Pat. No. 7,783,354 (Gunderson, et al.), both incorporated herein by reference in its entirety.

In one example, the peak amplitudes of consecutively sensed events may be determined from the cardiac electrical signal used to sense the events or from a filtered cardiac electrical signal determined from the raw cardiac electrical signal. For example, the maximum peak amplitude of the filtered cardiac electrical signal for each of the sensed events may be determined. A threshold may be defined based on the maximum peak amplitudes determined for the sensed events from the filtered cardiac signal. The maximum peak amplitudes may then be compared to the threshold, and events having a peak amplitude of the filtered cardiac electrical signal exceeding the threshold may be classified as R-waves. Events having a peak amplitude less than the threshold may be classified as T-waves. If T-waves are being sensed from the raw cardiac electrical signal, e.g., if the control module 80 has received an R-wave sensed event signal from the electrical sensing circuit 86 coinciding in time with an event classified as a T-wave, T-wave oversensing is detected at block 404.

Cardiac oversensing due to R-wave double counting may be avoided in most cases by setting a post-ventricular absolute blanking period that is applied by electrical sensing circuit 86 when an R-wave sensed event signal is produced. A sensing threshold crossing within the absolute blanking period is ignored so that the same R-wave is not sensed twice. R-wave double counting can still occur under some circumstances, e.g., when a single R-wave has two peaks or is particularly wide so that a second sensing threshold crossing occurs after the blanking period. Two sensed event signals may be produced by electrical sensing circuit 86 for the same R-wave.

To analyze the sensed events during the NST episode for R-wave double counting at block 402, the control module 80 may determine RR intervals between R-wave sensed event signals received from electrical sensing module 96. The length and pattern of RR intervals are analyzed to detect evidence of R-wave double counting. For example, if an alternating pattern of a very short RR interval, e.g., less than 160 ms, followed by a relatively longer RR interval, e.g., greater than 200 ms, is detected, R-wave double counting may be detected at block 405. The above-incorporated '354 patent (Gunderson et al.) generally discloses techniques that may be used for detecting R-wave double counting.

If TWOS is detected at block 404 or if R-wave double counting is detected at block 405, based on the analysis of the NST episode at block 402, non-lead related oversensing is identified and the non-lead related oversensing criteria are satisfied at block 410. The NST component of the lead issue detection criteria is not satisfied and therefore a LIA is withheld as described above in conjunction with FIG. 3.

If cardiac signal oversensing is not identified at blocks 404 and 405, the NST episode is analyzed for non-cardiac, non-lead related noise at block 406. Specifically, the cardiac electrical signal during the NST episode may be analyzed for the presence of EMI and/or myopotential noise in some examples. This analysis may include analyzing segments of the cardiac electrical signal between sensed events to determine baseline noise or fluctuations between sensed events. A fluctuation of the cardiac electrical signal during a time window between sensed events may be identified by computing a moving average of cardiac signal data points, e.g., 16 data points, and determining a threshold based on the moving average. For example, the threshold may be set to half of the moving average. When the filtered, rectified cardiac electrical signal crosses the threshold, a noise counter may be increased to provide an indication of the number of signal fluctuations occurring between events. In one example, a count of fluctuations of the cardiac electrical signal between sensed cardiac events that occur at least during the NST episode is determined, and oversensing of non-lead related noise is detected at block 408 if a threshold count is reached.

In another example, control module 80 detects non-cardiac, non-lead related oversensing by determining differences between sample points of the cardiac electrical signal at least during the detected NST episode and comparing the magnitude and sign of the differences to non-lead related noise criteria. If the non-lead related noise criteria are satisfied, oversensing due to non-lead related noise is detected. For instance, noise units in the cardiac electrical signal may be counted by control module 80. Each noise unit may be defined as two consecutive sample points that differ by more than a threshold amplitude difference, e.g., 3 A/D units, and represent a change in amplitude direction of the cardiac electrical signal. The number of noise units over a predetermined number of cardiac electrical signal sample points or selected time interval may be counted and compared to a noise threshold defined for detecting myopotential and/or EMI noise. The noise threshold may be defined as a percentage of all sample points. Myopotential noise may be characterized by a lower percentage of sample points being included in noise units than EMI so for the purposes of identifying non-cardiac, non-lead related noise, a single noise threshold may be used, above which myopotential noise and/or EMI is likely present. Examples of detecting myopotential noise and EMI based on a determination of noise units of the cardiac electrical signal are generally disclosed in the above-incorporated '354 patent (Gunderson).

If non-cardiac, non-lead related noise such as EMI or myopotential noise is not identified at block 408, non-lead related oversensing is not identified at block 412. The current NST episode meeting the oversensing criteria applied to sensed event intervals (as determined at block 308 of FIG. 4) may be used toward satisfying the lead issue detection criteria and triggering a LIA. The control module is configured to generate the lead integrity alert when a threshold number of detected NST episodes are determined to satisfy the oversensing criteria without satisfying the non-lead related oversensing criteria. If EMI or myopotential noise is detected at block 408, non-lead related oversensing during the NST episode is identified at block 410. The NST episode will not be used toward satisfying requirements for triggering a LIA. Control module 80 will withhold the LIA.

It is recognized that the analysis performed at block 402 for detecting cardiac oversensing and the analysis performed at block 406 for detecting non-cardiac, non-lead related oversensing may be performed simultaneously or in a different sequence than the sequence shown in FIG. 5. In general, after detecting an NST episode that satisfies event interval-based oversensing criteria, sensed event amplitude, waveform morphology analysis, and/or baseline analysis of the cardiac electrical signal acquired during the detected NST episode is performed to identify non-lead related oversensing. The identification of cardiac-related oversensing or the identification of non-cardiac, non-lead related oversensing during an NST episode in which sensed event intervals have already satisfied the oversensing criteria results in the NST episode not being used toward satisfying requirements for triggering the LIA.

Figure 6:
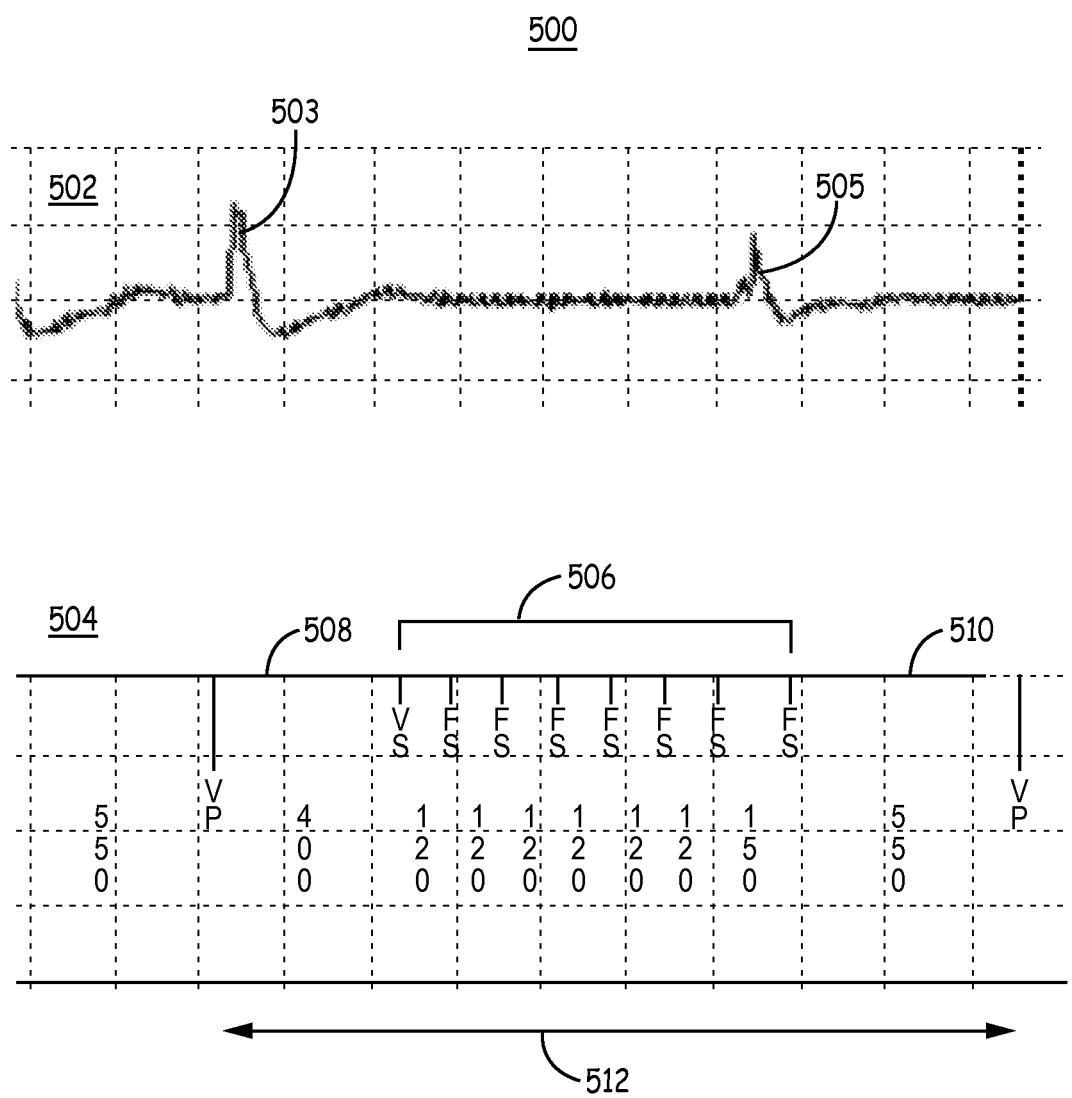
FIG. 6 is a timing diagram including a sample cardiac electrical signal and a marker channel signal.

FIG. 6 is a timing diagram 500 including a sample cardiac electrical signal 502 and a marker channel signal 504. The cardiac electrical signal depicts two R-waves 503 and 505.

The marker channel 504 includes ventricular pacing pulse markers, labeled "VP," one ventricular sensed event marker, labeled "VS," and fibrillation sensed event markers, labeled "FS." The FS event markers label sensed events that end sensed cardiac events intervals that are shorter than the tachyarrhythmia detection interval threshold and are counted for detecting tachyarrhythmia.

The VS event and seven consecutive FS events define seven consecutive tachyarrhythmia intervals that are detected as an NST episode 506. If the NST episode 506 meets oversensing criteria, control module 80 further analyzes NST episode 506 for cardiac oversensing and for non-cardiac, non-lead related oversensing. In some examples, a time interval 512 that encompasses NST episode 506 and at least one event interval 508 preceding the NST episode 506 and/or at least one event interval 510 immediately following NST episode 506 are analyzed for non-lead related oversensing. The event intervals 508 and 510 preceding and succeeding the NST episode 506 are not necessarily sensed event intervals. In the example shown, intervals 508 and 510 are defined by a starting or ending pacing pulse (VP).

Control module 80 may determine if a noise count, e.g., used to count signal fluctuations during event intervals or to count noise units as described above, has reached a threshold during time interval 512 that includes event intervals 508 and 510 immediately preceding and succeeding NST episode 506. If a noise threshold for detecting non-lead related noise such as EMI or myopotential noise is reached during time interval 512, non-lead related oversensing criteria are satisfied. NST episode 506 does not count toward satisfying requirements for triggering a LIA.

Figure 7:
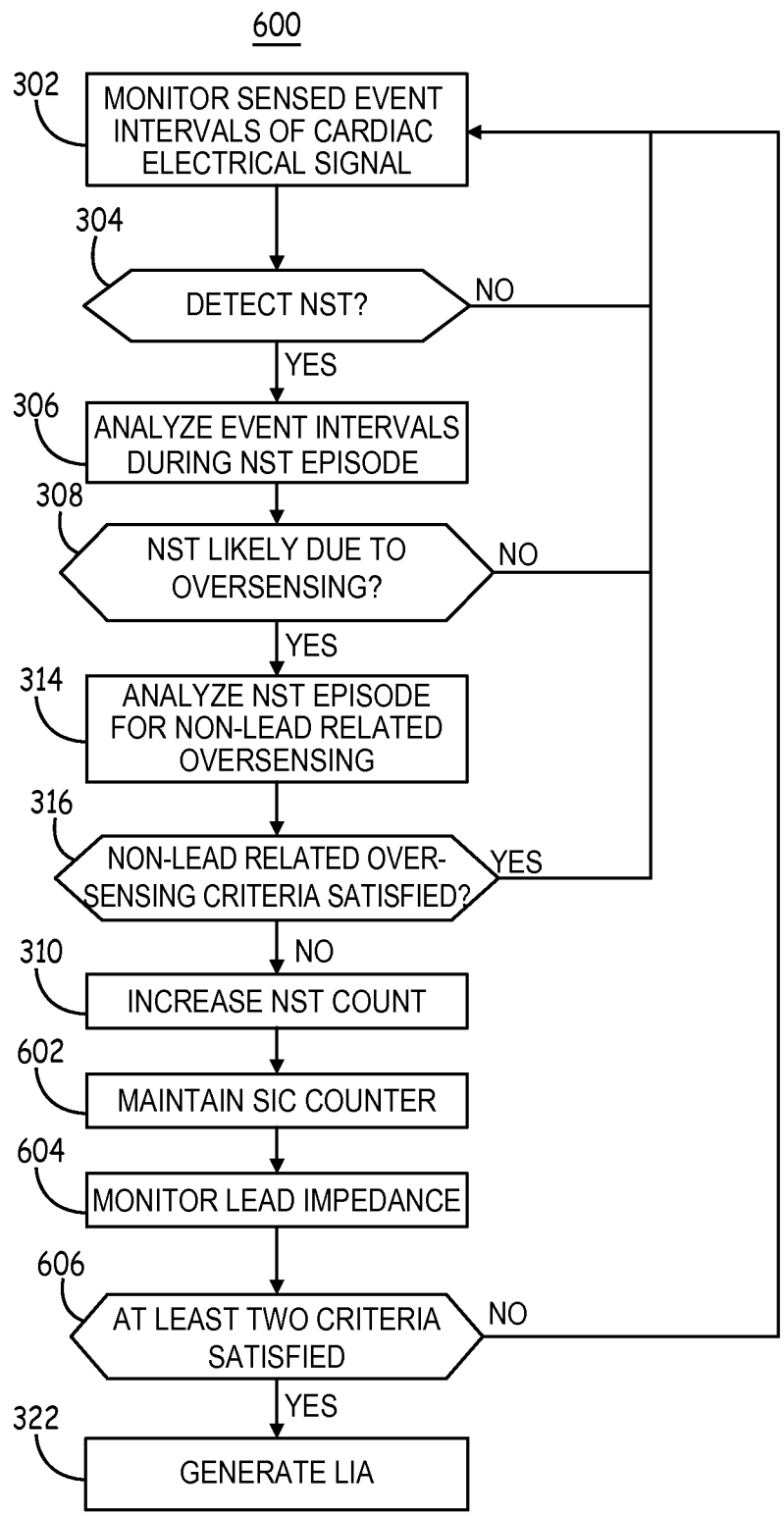
FIG. 7 is a flow chart of another example method for detecting a lead issue and generating a LIA based at least on detection and analysis of NST episodes.

FIG. 7 is a flow chart 600 of another example method for detecting a lead issue and generating a LIA based at least on detection and analysis of NST episodes. The blocks of flow chart 600 having the same reference number as blocks of flow chart 300 of FIG. 4 are not repeated in detail for sake of brevity, but the description of those blocks is equally applicable to the like numbered boxes of flow chart 600.

At block 302, control module 80 determines intervals between cardiac events within sensed cardiac electrical signals received from sensing circuit 86. The sensed event intervals are monitored at block 302 to determine if an NST is detected at block 304 according to NST detection criteria described in detail above. If the NST detection criteria are not satisfied, the control module 80 continues to monitor the sensed event intervals at block 302.

In response to detecting an NST episode at block 304, control module 80 may analyze the sensed event intervals during the NST episode at block 306 to determine whether the NST is likely caused by oversensing. If the event intervals meet the oversensing criteria, as determined at block 308, control module 80 further analyzes the cardiac electrical signal acquired during the NST episode at block 314 to rule out the presence of non-lead related oversensing. If the non-lead related oversensing criteria are not satisfied at block 316, control module 80 increases an NST counter at block 310. The NST episodes that satisfy the oversensing criteria applied at block 308 and do not satisfy the non-lead related oversensing criteria at block 316 are counted toward the NST component of the lead issue detection criteria. If the non-lead related oversensing criteria are satisfied at block 316, control module 80 continues to monitor sensed event intervals of the cardiac electrical signal at block 302.

The lead issue detection criteria may also include other components in addition to the NST component. In one example, lead issue detection criteria may include another oversensing component and lead impedance component. To this end, control module 80 measures metrics associated with any other components of the lead issue detection criteria. In the example of FIG. 7, control module maintains a short interval counter (SIC) at block 602 (which is another oversensing component of the lead issue detection criteria) and monitors a lead impedance at block 604 (which is a lead impedance component of the lead issue detection criteria).

In one embodiment, control module 80 may maintain the SIC at block 602 in the manner described in FIG. 11 of U.S. Pat. No. 7,289,851 (Gunderson et al.), the description of FIG. 11 is incorporated herein by reference in its entirety. The control module may analyze an RR-interval to determine whether the RR-interval is less than a predetermined threshold SIC interval. In one example, the predetermined threshold SIC interval is a predetermined time period above the blanking period, such as 20 ms above the blanking period. The SIC is incremented each time the current RR-interval is determined to be less than the predetermined SIC threshold interval.

Control module 80 may monitor lead impedance at block 604 in any of a number of ways. In some instances, control module 80 may monitor for any impedance measurement that is outside of a "normal" impedance range. For example, control module 80 may compare a lead impedance measurement taken at a particular point in time to a fixed range of acceptable values or a fixed reference value, such as disclosed for example in U.S. Pat. No. 6,317,633 (Jorgenson et al.), which is incorporated herein by reference in its entirety. In other instances, control module 80 may monitor impedance trends over one or more periods of time, e.g., a short term impedance trend and/or a long term impedance trend. For example, control module 80 may monitor lead impedance at block 604 as described in U.S. Pat. No. 7,289,851 (Gunderson et al.), which is incorporated herein by reference in its entirety.

Control module 80 determines whether at least two of the components of the lead issue detection criteria (e.g., the NST, the SIC, and the lead impedance components) are met at block 606. As described above, the NST component of the lead issue detection criteria is met when the NST count reaches a NST threshold within a particular period of time. Likewise, the SIC component of the lead issue detection criteria is met when the SIC value reaches a SIC threshold within a particular period of time. In one particular example, the SIC component may be met when the counter is greater than or equal to thirty within three days. The lead impedance criteria may be met when at least one lead impedance value is outside of an acceptable "normal" impedance range and/or when a long term or short term impedance is determined to be abnormal. When at least two of the components of the lead issue detection criteria are met, a LIA is generated at block 322.

Thus, various examples of medical device apparatus and associated methods have been described for avoiding false lead issue detections and false LIA generation. One of ordinary skill in the art will appreciate that various modifications may be made to the described embodiments without departing from the scope of the following claims.

The invention claimed is:

1. An implantable medical device comprising:
  a sensing circuit configured to receive a cardiac electrical signal and sense cardiac events within the cardiac electrical signal, the cardiac electrical signal received via electrodes carried by a medical electrical lead when the medical electrical lead is coupled to the implantable medical device; and a control module coupled to the sensing circuit and configured to:
  determine a plurality of sensed event intervals, each of the plurality of sensed event intervals being a time interval between two consecutive ones of the sensed cardiac events;
  detect a non-sustained tachyarrhythmia (NST) episode based on at least a portion of the sensed event intervals;
  determine if the sensed event intervals satisfy an oversensing criteria;
  when the sensed event intervals satisfy the oversensing criteria, compare the detected NST episode to non-lead related oversensing criteria;
  ignore the NST episode for purposes of determining whether to generate a lead integrity alert when the non-lead related oversensing criteria are satisfied;
  use the NST episode as part of an NST component of a lead issue detection criteria when the non-lead related oversensing criteria are not satisfied;
  determine that the NST component of the lead issue detection criteria is met; and
  generate the lead integrity alert when the NST component of the lead issue detection criteria is met.

2. The device of claim 1, wherein the control module is configured to determine if the sensed event intervals satisfy the oversensing criteria by determining at least one metric of the sensed event intervals that occur during the detected NST episode and comparing the metric to a threshold, the metric comprising one of a maximum, a minimum, a range, or an average of the sensed event intervals during the NST episode.

3. The device of claim 1, wherein the control module determines that the NST component of the lead issue detection criteria is met when a threshold number of detected NST episodes are determined to satisfy the oversensing criteria and do not satisfy the non-lead related oversensing criteria.

4. The device of claim 3, wherein the lead issue detection criteria includes at least one of a lead impedance component and an oversensing component in addition to the NST component, wherein the control module is configured to generate the lead integrity alert when the NST component and at least one of the lead impedance component and the oversensing component are met.

5. The device of claim 4, wherein the oversensing component comprises a short interval counter and the control module is configured to determine that the oversensing component is met when a value the short interval counter exceeds a threshold value within a predetermined time period.

6. The device of claim 4, wherein the control module is configured to determine that the lead impedance component of the lead issue detection criteria is met when at least one lead impedance value is outside of an acceptable range of impedances.

7. The device of claim 4, wherein the control module is configured to determine that the lead impedance component of the lead issue detection criteria is met based on at least one of a long term impedance trend and a short term impedance trend.

8. The device of claim 1, wherein the control module is configured to compare the detected NST episode to non-lead related oversensing criteria by analyzing a plurality of the sensed events that occur during the detected NST episode to determine if the sensed events during the detected NST episode include a T-wave.

9. The device of claim 1, wherein the control module is configured to compare the detected NST episode to non-lead related oversensing criteria by determining if the sensed event intervals that occur during the detected NST episode include a double-counted R-wave.

10. The device of claim 1, wherein the control module is configured to compare the detected NST episode to non-lead related oversensing criteria by:
  determining a count of fluctuations of the cardiac electrical signal during at least one sensed event interval that occurs during the NST episode; and
  detecting non-lead related oversensing when the count of fluctuations of the signal within the time window reaches a noise threshold.

11. The device of claim 1, wherein the control module is configured to compare the detected NST episode to non-lead related oversensing criteria by:
  determining differences between sample points of the cardiac electrical signal during the detected NST episode;
  comparing the magnitude and sign of the differences to non-lead related noise criteria; and
  detecting non-lead related oversensing when a threshold number of the differences satisfy the non-lead related noise criteria.

12. The device of claim 1, wherein the control module is configured to compare the detected NST episode to non-lead related oversensing criteria by:
  determining a noise count from the cardiac electrical signal; and
  detecting non-lead related oversensing when the noise count reaches a noise threshold during a time interval that includes the detected NST episode and at least one of an event interval immediately preceding the NST episode and an event interval immediately succeeding the NST episode.

13. The device of claim 1, wherein the control module is further configured to:
  increase a counter in response to detecting the NST episode and determining that the oversensing criteria are met;
  compare the counter to a lead issue detection threshold; and
  compare the detected NST episode to the non-lead related oversensing criteria after the counter reaches the lead issue detection threshold.

14. The device of claim 1, wherein the control module is further configured to:
  compare a preceding NST episode that satisfied the oversensing criteria to the non-lead related oversensing criteria in response to the detected NST episode satisfying the oversensing criteria and not satisfying the non-lead related oversensing criteria; and
  maintain a counter at a current value in response to the preceding NST episode satisfying the non-lead related oversensing criteria.

15. The device of claim 1, wherein the control module is configured to take corrective action in response to the lead issue detection criteria being met.

16. The device of claim 1, further comprising a telemetry module configured to generate the alert by transmitting a wireless communication signal.

17. A method comprising:
  sensing events from the cardiac electrical signal by a sensing module of an implantable medical device, the cardiac electrical signal received via electrodes carried by a medical electrical lead when the medical electrical lead is coupled to the implantable medical device;

determining by a control module of the implantable medical device a plurality of sensed event intervals, each of the plurality of sensed event intervals being a time interval between two consecutive ones of the sensed events;

detecting a non-sustained tachyarrhythmia (NST) episode based on at least a portion of the sensed event intervals;

determining if the sensed event intervals of the NST episode satisfy oversensing criteria;

when the sensed event intervals satisfy the oversensing criteria:
  comparing the detected NST episode to non-lead related oversensing criteria;
  ignoring the NST episode for purposes of determining whether to generate a lead integrity alert when the non-lead related oversensing criteria are satisfied; and
  using the NST episode as part of an NST component of a lead issue detection criteria when the non-lead related oversensing criteria are not satisfied;
  determining that the NST component of the lead issue detection criteria is met; and
  generating the lead integrity alert when the NST component of the lead issue detection criteria is met.

18. The method of claim 17, wherein determining if the sensed event intervals satisfy the oversensing criteria comprises determining at least one metric of the sensed event intervals that occur during the detected NST episode and comparing the metric to a threshold, the metric comprising one of a maximum, a minimum, a range, or an average of the sensed event intervals during the NST episode.

19. The method of claim 17, wherein determining that the NST component of the lead issue detection criteria is met comprises determining that the NST component of the lead issue detection criteria is met when a threshold number of detected NST episodes are determined to satisfy the oversensing criteria and to not satisfy the non-lead related oversensing criteria.

20. The method of claim 17, wherein the lead issue detection criteria includes at least one of a lead impedance component and an oversensing component in addition to the NST component, wherein generating the lead integrity alert comprises generating the lead integrity alert when the NST component and at least one of the lead impedance component and the oversensing component are met.

21. The method of claim 20, wherein the oversensing component comprises a short interval counter, the method further comprising determining that the oversensing component is met when a value the short interval counter exceeds a threshold value within a predetermined time period.

22. The method of claim 20, further comprising determining that the lead impedance component of the lead issue detection criteria is met when at least one measured lead impedance value is outside of an acceptable range of impedances.

23. The method of claim 17, wherein comparing the detected NST episode to non-lead related oversensing criteria comprises analyzing a plurality of the sensed events that occur during the detected NST episode to determine if the sensed events during the detected NST episode include any one of a T-wave and a double-counted R-wave.

24. The method of claim 17, further comprising:
  increasing a counter in response to detecting the NST episode and determining that the oversensing criteria are met;
  comparing the counter to a lead issue detection threshold; and
  comparing the detected NST episode to the non-lead related oversensing criteria after the counter reaches the lead issue detection threshold.

25. The method of claim 17, further comprising:
  comparing a preceding NST episode that satisfied the lead-related oversensing criteria to the non-lead related oversensing criteria in response to the detected NST episode satisfying the oversensing criteria and not satisfying the non-lead related oversensing criteria; and
  maintain an NST counter at a current value in response to the preceding NST episode satisfying the non-lead related oversensing criteria.

26. The method of claim 17, further comprising taking corrective action in response to the lead issue detection criteria being met.

27. The method of claim 17, further comprising transmitting a wireless telemetry signal in response to the lead issue detection criteria being met.

\* \* \* \* \*